| United States Patent [19] | [11] Patent Number: 4,650,609 |
| Brittelli | [45] Date of Patent: Mar. 17, 1987 |

[54] TETRAPHOSPHINYLQUINODIMETHANES

[75] Inventor: David R. Brittelli, Nottingham, Pa.

[73] Assignee: E. I. Du Pont de Nemours and Company, Wilmington, Del.

[21] Appl. No.: 748,661

[22] Filed: Jun. 25, 1985

[51] Int. Cl.$^4$ .............................. C07F 9/40; C07F 9/42
[52] U.S. Cl. ............................ 260/396 N; 260/502.4 P; 260/543 P; 556/18; 556/405; 558/77; 558/162
[58] Field of Search ............... 260/396 N, 502.4 P, 260/543 P; 558/77, 162; 556/405, 18

[56] References Cited

U.S. PATENT DOCUMENTS 4,444,930  4/1984  Guerin et al. ........................ 524/125

OTHER PUBLICATIONS

*Synthesis,* 309–311 (1978), Comins et al.
*Chem. Ber.,* 88:195–198 (1955), Kreutzkamp.
*J. Gen. Chem. of USSR,* 27:1683–1688 (1957), Pudovik et al.
*Organic Phosphorus Compounds,* vol. 7, Wiley Interscience, New York, 1976, pp. 34–35 (Kosolapoff and Maier, eds.).

*Primary Examiner*—Anton H. Sutto

[57]  ABSTRACT

Compounds having a quinodimethane or a 7,8-dihydroquinodimethane nucleus and four substituted phosphinyl groups at the 7- and 8-positions are disclosed. A process for preparing the specified compounds is also disclosed.

8 Claims, No Drawings

TETRAPHOSPHINYLQUINODIMETHANES

FIELD OF THE INVENTION

This invention relates to tetraphosphinylquinodimethane compounds and structurally-related derivatives which are useful as lithium sequestering agents.

BACKGROUND OF THE INVENTION

Comins et al., Synthesis, 309 (1978), discloses the preparation of phosphonate esters by treatment of active methylene compounds with diethyl phosphorochloridate. More specifically, the authors describe the phosphorylation of cyano- and sulfur-stabilized carbanions. Kreutzkamp, Chem. Ber., 88:195 (1955) discloses the phosphorylation of ethyl acetate and diethyl malonate enolate with diethyl chlorophosphate. The product of the latter reaction is now known to be an enol phosphate, not a phosphonate. Pudovik et al., Zh. Obshch. Khim., 27:1611 (1957) describes the phosphorylation of diethyl malonate and acetylacetone enolate with diethyl chlorophosphate. The products of these reactions are now known to be enol phosphates. Organic Phosphorus Compounds (Kosolapoff and Maier eds.) Vol. 7, Wiley Interscience, New York, 1976, pp 34–35, describes the phosphorylation of carbon with phosphoric acid ester halides.

SUMMARY OF THE INVENTION

The present invention provides compounds of the formula

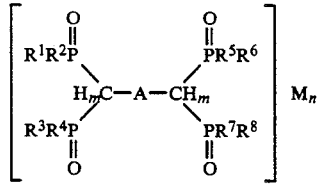

wherein

A is 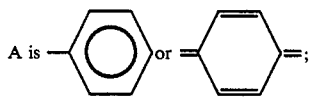 ;

$R^1$, $R^2$, $R^3$, $R^4$, $R^5$, $R^6$, $R^7$, and $R^8$ are individually selected from the group consisting of —F, —Cl, —OH, —OSi(CH$_3$)$_3$, and —OC$_z$H$_{2z+1}$;

and, taken in combination, $R^1$ and $R^2$, $R^3$ and $R^4$, $R^5$ and $R^6$, and $R^7$ and $R^8$ are individually selected from the group consisting of —O(CH$_2$)$_2$O— and —O(CH$_2$)$_3$O—;

provided that, where any two members of $R^1$ through $R^8$ which are attached to the same phosphorus atom are different, said members are —OC$_z$H$_{2z+1}$;

M is Li, Na, K, Rb;

m is 0 or 1; provided that, where A is

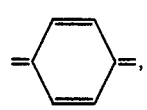

m is 0;

n is 0 where m is 1, 2 where m is 0 and A is

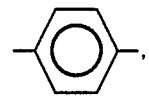

and 0 or 1 where A is

and z is an integer from 2 to 8, inclusive. In addition, the present invention provides a process for preparing the specified compounds.

DETAILED DESCRIPTION OF THE INVENTION

The tetraphosphinylquinodimethanes and structurally-related derivatives of the present invention are compounds of the formula

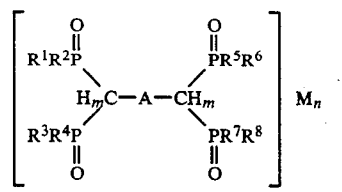

wherein

A, $R^1$ through $R^8$, M, m, n, and z are as previously defined. Preferably, moieties $R^1$ and $R^2$, $R^3$ and $R^4$, $R^5$ and $R^6$, and $R^7$ and $R^8$ are the same and, most preferably, $R^1$ through $R^8$ are the same. Preferably, moieties $R^1$ through $R^8$ are alkoxy groups having from 2 to 8 carbon atoms and, most preferably, ethoxy. Preferably, moiety M is lithium, m is 0, and n is 1. The compounds of the invention are useful as lithium sequestering agents.

As used herein, "tetraphosphinylquinodimethane compound" means a compound having the formula

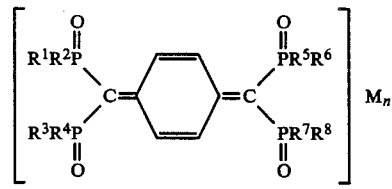

and "tetraphosphinyldihydroquinodimethane compound" means a compound having the formula

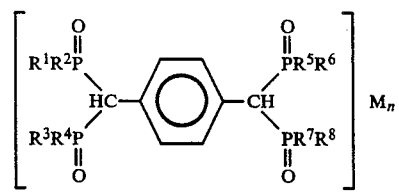

wherein $R^1$ through $R^8$, M, m, n, and z are as previously defined.

Octaalkoxy derivatives of tetraphosphinyldihydroquinodimethanes of the present invention can be prepared by phosphorylating p-xylylenebis(phosphonates) having the formula

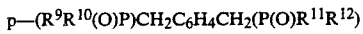

p—$(R^9R^{10}(O)P)CH_2C_6H_4CH_2(P(O)R^{11}R^{12})$ where $R^9$, $R^{10}$, $R^{11}$, and $R^{12}$ are alkoxy groups having from 2 to 8 carbon atoms. A p-xylylenebis(phosphonate) is contacted sequentially with an anionic base and a sterically-hindered secondary amide to remove at least one proton from each of the benzylic methylene groups. Resulting anions are contacted with at least one phosphorylating agent having the formula $R^{13}R^{14}(O)PX$, where X is —F, —Cl, or —OPR$^{15}$R$^{16}$ and $R^{13}$, $R^{14}$, $R^{15}$, and $R^{16}$ are alkoxy groups having from 2 to 8 carbon atoms. One proton removed from each of the benzylic methylene groups is replaced by a substituted phosphinyl group from the selected phosphorylating agent to form certain compounds of the present invention having a 7,8-dihydroquinodimethane nucleus and four substituted phosphinyl groups at the 7- and 8-positions. These compounds can be converted to form other tetraphosphinyldihydroquinodimethane compounds of the present invention by techniques known in the art. Also, the tetraphosphinyldihydroquinodimethanes can be oxidized in a specified manner to form tetraphosphinylquinodimethane compounds and tetraphosphinylquinodimethane radical anion salts of the present invention.

Preparation of Tetraphosphinyldihydroquinodimethanes

Octaalkoxy derivatives of tetraphosphinyldihydroquinodimethanes can be prepared in a five-step process wherein a p-xylylenebis(phosphonate) is contacted sequentially with (1) an anionic base, (2) a phosphorylating agent, (3) a sterically-hindered secondary amide, (4) a phosphorylating agent and (5) an anhydrous acid. The five-step process is conducted in an organic solvent capable of dissolving p-xylylenebis(phosphonate), anionic intermediates, and products. Preferably, the process is conducted under anhydrous conditions and the solvent is tetrahydrofuran. Most preferably, the process is conducted under dry nitrogen or argon gas to prevent oxidation and hydrolytic side reactions resulting from contamination with atmospheric oxygen and moisture.

In the five-step process, a p-xylylenebis(phosphonate) having the formula

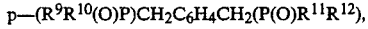

p—$(R^9R^{10}(O)P)CH_2C_6H_4CH_2(P(O)R^{11}R^{12})$, where $R^9$ to $R^{12}$, inclusive, are alkoxy groups having from 2 to 8 carbon atoms, is contacted with sufficient anionic base in a suitable organic solvent to remove two protons from the bis(phosphonate) and form a p-xylylenebis(phosphonate)diide. Preferably, $R^9$ to $R^{12}$, inclusive, are ethoxy. The p-xylylenebis(phosphonate) can be prepared from commercially available materials by the method of Chantrell et al., *J. Appl. Chem.* 15:460 (1965), the disclosure of which is incorporated herein by reference. Other methods of preparing the p-xylylenebis(phosphonate) are known in the art. Suitable anionic bases are strong enough to form the anion of the bis(phosphonate) which has a pKa of about 25. A partial list of suitable anionic bases includes alkyl and aryl lithium compounds and lithium amides selected from the group consisting of lithium di-isoproply amide, lithium 2,2,6,6-tetramethylpiperidide, lithium di-isobutylamide, lithium 2,5-dimethylpyrrolidide, and lithium bis(trimethylsilyl)amide. Other suitable anionic bases are known to one skilled in the art. Preferably, selected anionic bases are in the form of their lithium salts. The lithium solubilizes intermediates in the process and facilitates the reaction. Most preferably, the anionic base is n-butyl lithium. The reaction can be conducted at a temperature from about −100° C. to 35° C., but preferably from about −78° C. to −20° C.

The resulting p-xylylenebis(phosphonate)diide is contacted with at least one phosphorylating agent having the formula $R^{13}R^{14}(O)PX$ wherein X is —F, —Cl, or —OP(O)$R^{15}R^{16}$ and $R^{13}$ to $R^{16}$, inclusive, are alkoxy groups having from 2 to 8 carbon atoms and, preferably, ethoxy, to form a mixture. Phosphorylating agents having the formula $(R^{13}R^{14}(O)P)O(P(O)R^{15}R^{16})$ where $R^{13}$ to $R^{16}$, inclusive, are alkoxy groups having 2 to 8 carbon atoms can be prepared from commercially available materials by the method of Toy, *J. Amer. Chem. Soc.*, 70:3882 (1948), the disclosure of which is incorporated herein by reference. These tetraalkyl pyrophosphates can be converted to form other specified phosphorylating agents by techniques known in the art. Preferably, the p-xylylenebis(phosphonate)diide is contacted with an equimolar amount of tetraalkyl pyrophosphate. In a preferred embodiment of the five-step process, the resulting combination is warmed to ambient temperature to increase the rate of reaction and then cooled to −78° C.

The resulting mixture is contacted with sufficient of a sterically-hindered secondary amide to form a mixture of diphosphorylated, triphosphorylated, and tetraphosphorylated dianions. Suitable sterically-hindered secondary amides are strong enough to form the diphosphonate dianion which has a pKa of about 25. A partial list of suitable sterically-hindered secondary amides includes compounds selected from the group consisting of lithium di-isopropyl amide, lithium 2,2,6,6-tetramethylpiperidide, lithium di-isobutylamide, lithium 2,5-dimethylpyrrolidide, and lithium bis(trimethylsilyl)amide. Other suitable amides are known to one skilled in the art. Preferably, selected amides are in the form of their lithium salts. Most preferably, the amide is 2,2,6,6-tetramethylpiperamide. Preferably, the mixture of anions is prepared with two molar equivalents of the selected anion.

The resulting mixture of anions is contacted with at least one of the previously defined phosphorylating agents to form an octaalkyl 1,4-phenylenebis(methylidyne)tetrakis(phosphonate)dianion which is contacted with an anhydrous acid to form the corresponding octaalkoxy tetraphosphinyldihydroquinodimethane. A partial list of suitable anhydrous acids includes alkanoic acids and dialkyl phosphoric acids. Preferably, the octaalkoxy tetraphosphinyldihydroquinodimethane is prepared from a reaction mixture containing the octaalkyl 1,4-phenylenebis(methylidyne)tetrakis-(phosphonate)dianion by (1) removing the organic solvent, (2) treating the resulting residue with ether to cause crystallization, (3) decanting the ether, (4) dissolving the solid in tetrahydrofuran, and (5) acidifying the resulting combination to neutrality with an anhydrous acid, preferably dialkyl phosphoric acid. The octaalkoxy tetraphosphinyldihydroquinodimethane can be isolated from the resulting combination by (1) removing the tetrahydrofuran under reduced pressure, (2) treating the resulting residue with ether to cause crystallization, (3) filtering the resulting solid and (4) extracting multiply with ether. The resulting ether extracts can be evaporated to give the tetraphosphinyldihydroquinodimethane which can be purified, if desired, by techniques well-known in the art, like crystallization.

Octaalkoxy species can be converted to other tetraphosphinyldihydroquinodimethanes by techniques known in the art. Octa(trimethylsilyl)esters can be prepared by contacting the octaalkoxy species with bromotrimethylsilane by the method of McKenna et al., *Tetrahedron Lett.*, 155 (1977). Tetraphosphonic acids can be prepared by contacting the silyl esters with water or alcohols by the method of Rabinowitz, *J. Org. Chem.*, 28:2975 (1963). The silyl esters can be contacted with oxalyl chloride to form the corresponding tetrakis(phosphonylodichlorides). The phosphonyl dichlorides can be converted into octamethoxy and tetra(alkylene dioxy) species by methods known in the art, like those described in *Organic Phosphorus Compounds* (Kosolapoff and Maier eds.) Vol. 7, Wiley Interscience, New York, 1976, p. 22. The phosphonyl dichlorides also serve as intermediates to corresponding phosphonyl difluorides by methods known in the art, like those described in *Organic Phosphorus Compounds*, Vol. 4, p. 163.

Preparation of tetraphosphinylquinodimethanes

Tetraphosphinylquinodimethanes of the present invention can be prepared from the tetraphosphinyldihydroquinodimethanes, described above, in a two-step process. A tetraphosphinyldihydroquinodimethane is contacted with at least one non-lithium anionic base, such as potassium amide and potassium hydride, but preferably potassium hydride, to form a 1,4-phenylenebis(methylidyne)tetrakis(phosphonate)diide. The diide is oxidized with at least one electron acceptor having a half wave oxidation potential more positive that about −0.20 volts to form a quinodimethane. Suitable electron acceptors are known to one skilled in the art. Preferably, the electron acceptor is selected from the group consisting of ferricinium salts and 7,7,8,8-tetracyanoquinodimethane. Most preferably, the electron acceptor is (trimethylammoniomethyl)ferricinium bis(tetrafluoroborate) because it is easily separated from the quinodimethanes on the basis of solubility properties. Preferably, the oxidation is conducted under anhydrous conditions in an oxygen-free atmosphere in a nonprotic solvent, such as tetrahydrofuran or 1,2-dimethoxyethane, at about ambient temperature. The resulting quinodimethane can be purified by techniques well-known in the art, such as crystallization. Preferably, the oxidation reaction is conducted with two moles of the selected anionic base and the selected electron acceptor per mole of the dihydroquinodimethane.

Preparation of Tetraphosphinylquinodimethane Radical Anion Salts

Tetraphosphinylquinodimethane radical anion salts of the present invention can be prepared from the tetraphosphinyldihydroquinodimethanes, described above, in a two-step process. A tetraphosphinyldihydroquinodimethane is contacted with at least one anionic base, such as potassium amide and potassium hydride, but preferably potassium hydride, to form a 1,4-phenylenebis(methylidyne)tetrakis(phosphonate)diide. The diide is oxidized with at least one molar equivalent of an electron acceptor having a half wave oxidation potential more positive than about −0.20 volts to form a quinodimethane radical anion salt. Suitable electron acceptors are selected from the group consisting of ferricinium tetrafluoroborate, ferricinium hexafluorophosphate, (trimethylammoniomethyl)ferricinium bis(tetrafluoroborate), and 7,7,8,8-tetracyanoquinodimethane. Other suitable electron acceptors would be apparent and available to one skilled in the art. Preferably, the oxidation is conducted under anhydrous conditions in an oxygen-free atmosphere in a nonprotic solvent with one mole or less of the selected anionic base and the selected electron acceptor per mole of dihydroquinodimethane.

The present invention is further described by the following examples, wherein all parts and percentages are by weight and degrees are Celsius.

EXAMPLE 1

Preparation of Octaethyl 1,4-Phenylenebis(methylidyne)tetrakis(phosphonate)(2) from Tetraethyl p-Xylylenebis(phosphonate)(1)

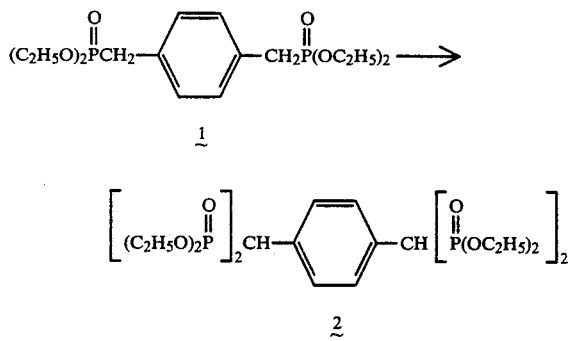

200 mL of dry tetrahydrofuran were added by syringe to 9.28 g of tetraethyl p-xylylenebis(phosphonate)(1) (24.5 mmol) in a 500 mL 3-neck flask equipped with a thermometer, septum, addition funnel, and mechanical stirrer under nitrogen. The resulting mixture was stirred briefly to dissolve the solid and cooled to −78°. 31 mL of a 1.6N solution of n-butyl lithium (49.6 mmol) in hexane were added to the mixture to form a homogeneous golden-yellow solution to which 6.0 mL of tetraethyl pyrophosphate (24.6 mmol) in 35 mL of tetrahydrofuran were added dropwise. The resulting combination was allowed to warm to 0°, cooled to −78°, and treated dropwise with a solution prepared by mixing 50 mL of tetrahydrofuran and 8.35 mL of 2,2,6,6-tetramethylpiperidine (49.5 mmol) with 31 mL of 1.6N n-butyl lithium (49.6 mmol) in hexane solution at −30°-40°. 6.0 mL of tetraethyl pyrophosphate (24.6 mmol) in 25 mL of tetrahydrofuran were then added to the flask dropwise. The resulting mixture was allowed to warm to 22°-25°. Another 6.0 mL of the tetraethyl pyrophosphate (24.6 mmol) were added to the flask and the resulting mixture was stirred until it was light yellow in color.

A 2 mL aliquot of the mixture was removed from the flask and treated with a dilute solution of iodine in tetrahydrofuran to give an intense green-colored solution. The solution was examined by electron spin resonance (esr) spectrometry which showed a 25-line pattern composed of a quintet of quintets ($a_P = 10.84$ G, $a_H = 1.53$ G, $g = 2.0027$). The pattern indicated that the green species was the radical anion of the quinodimethane bearing 4 equivalent protons and 4 equivalent phosphorus groups.

The remaining mixture was transferred by syringe to a 1 L single-neck round bottom flask equipped with a large magnetic stirring bar and a vacuum takeoff bearing a septum and stopcock under nitrogen. The tetrahydrofuran was removed from the solution under reduced pressure and the resulting residue was triturated three times with 300 mL portions of diethyl ether. Crystalline material remaining after removal of the last portion of ether was dried under a vacuum and dissolved in 75 mL of tetrahydrofuran. The resulting mixture was treated with sufficient diethyl phosphate to bring the mixture to about pH 7.

The tetrahydrofuran was then removed from the mixture under reduced pressure to leave a white crystalline residue. The residue was triturated with 100 mL of ether and filtered in a nitrogen pressure funnel with protection from atmospheric moisture. The filtrate in standing deposited 0.3 g of octaethyl 1,4-phenylenebis(-methylidyne)tetrakis(phosphonate)(2). The solid in the pressure funnel consisted of 14.3 g of octaethyl 1,4-phenylenebis(methylidyne)tetrakis(phosphonate)(2) complexed to lithium diethyl phosphate. The solid was extracted with boiling ether to give 5.524 g of octaethyl 1,4-phenylenebis(methylidyne)tetrakis(phosphonate)(2) which was purified by recrystallization from n-butyl chloride/petroleum ether, mp 126.5°–127.5°.

Ir(KBr wafer) 1255 (P=O) and 1025 (P—O—C) cm$^{-1}$; UV(C$_2$H$_5$OH)$\lambda_{max}(\epsilon)$ 223(20,000), 257(260), 263(327), and 273(268) nm; $^1$H nmr (CDCl$_3$) $\delta$1.16(12, t(J=7 Hz), one set of diastereotopic —OCH$_2$CH$_3$'s), 1.27(12, t(J=7 Hz), other set of diastereotopic —OCH$_2$CH$_3$'s), 3.75(2, t(J$_{PH}$=25 Hz), —CH(P(O)(OC$_2$H$_5$)$_2$)$_2$), 3.9–4.2 (16, m, OCH$_2$—), 7.47(4, s, aryl —H); $^{31}$P nmr (CDCl$_3$) $\delta$18.82; $^{13}$C nmr (CDCl$_3$) $\delta$16.07(s, CH$_3$), 45.25(t(J$_{PH}$=133 Hz), —H(P=O)$_2$), 62.90($\delta$(J$_{PH}$=10), —OCH$_2$), and 129.54, 129.67, and 130.39 (s, aryl C).

Anal.: Calcd. for C$_{24}$H$_{46}$O$_{12}$P$_4$: C, 44.31; H, 7.15. Found: C, 44.32; H, 7.18.

EXAMPLE 2

Preparation of Octakis(trimethylsilyl)1,4-Phenylenebis(methylidyne)-tetrakis(phosphonate)(7) from Octaethyl 1,4-Phenylenebis(methylidyne)tetrakis(phosphonate)(2)

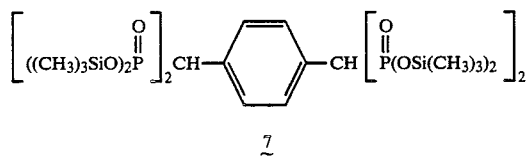

1.70 mL of bromotrimethylsilane (12.9 mmol) were added under nitrogen to 0.677 g of octaethyl 1,4-phenylenebis(methylidyne)tetrakis(phosphonate)(2) (1.04 mmol) prepared according to a procedure similar to that of Example 1. The resulting mixture was stirred for about one hour until all the solid had dissolved. Volatile materials were removed from the mixture under reduced pressure to leave 1.04 g of a crystalline product, octakis(trimethylsilyl)1,4-phenylenebis(methylidyne)tetrakis(phosphonate)(7) (1.04 mmol). $^1$H nmr (CDCl$_3$) $\delta$0.00(72,s, OSi(CH$_3$)$_3$), 3.33(2, t(J$_{PH}$=25), —CH(P=O)$_2$), and 7.20 (4, s, aryl —H).

EXAMPLE 3

Preparation of 1,4-Phenylenebis(methylidyne)tetrakis(phosphonic acid)(8) from Octakis(trimethylsilyl)1,4-Phenylenebis(methylidyne)-tetrakis(phosphonate)(7)

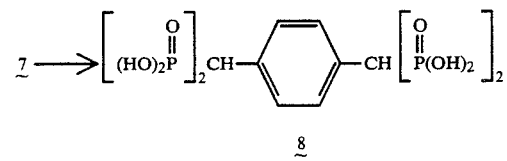

1.04 g of octakis(trimethylsilyl)1,4-phenylenebis(methylidyne)tetrakis(phosphonate)(7) (1.09 mmol), prepared according to a procedure similar to that of Example 2, were dissolved in 20 mL of methanol. The methanol was removed under reduced pressure and the resulting solid was dissolved in another 20 mL of methanol which was evaporated as before. The resulting product, 1,4-phenylenebis(methylidyne)tetrakis(phosphonic acid)(8) (0.443 g; 1.04 mmol), was a white powder which dissolved in water to give an acidic solution. $^1$H nmr (D$_2$O) $\delta$3.87 (2,t(J$_{PH}$=25 Hz), —CH(P=O)$_2$) and 7.28(4, s, aryl—H).

EXAMPLE 4

Preparation of 1,4-Phenylenebis(methylidyne)tetrakis(phosphonyldichloride)(9) from Octakis(trimethylsilyl)-1,4-Phenylenebis(methylidyne)-tetrakis(phosphonate)(7)

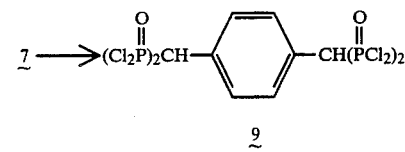

2.83 g of octakis(trimethylsilyl)1,4-phenylenebis(methylidyne)tetrakis(phosphonate)(7) (2.96 mmol), prepared according to a procedure similar to that of Example 2 from 1.863 g of octaethyl 1,4-phenylene-bis(methylidyne)tetrakis(phosphonate)(2) (2.9 mmol) and 5.0 mL of bromotrimethylsilane (37.9 mmol), were mixed with 10 mL of oxalyl chloride (120 mmol). The resulting mixture was stirred for one hour and treated with 3 drops of N,N-dimethylformamide. The resulting mixture was stirred for two hours, filtered, and dried under reduced pressure to give 1.72 g of a light yellow product, 1,4-phenylenebis(methylidyne)tetrakis(phosphonyldichloride)(9) (2.80 mmol), mp 185°d; $^1$H nmr(POCl$_3$) $\delta$5.93(2, t(J$_{PH}$=21 Hz), —CH(POCl$_2$)$_2$) and 7.87(4, s, aryl —H).

EXAMPLE 5

Preparation of Octaethyl 1,4-(2,5-cyclohexadienylidene)bis(methylene)tetrakis(phosphonate)(13) using 7,7,8,8-Tetracyanoquinodimethane as the Oxidant

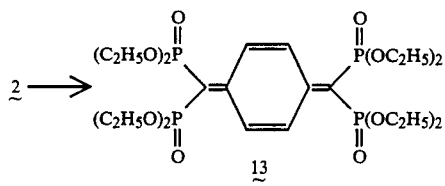

50 mL of dry, degassed tetrahydrofuran were added to 0.080 g potassium hydride (2 mmol) and 0.650 g octaethyl 1,4-phenylenebis(methylidyne)tetrakis(phosphonate)(2)(1 mmol). The resulting mixture was stirred for 2 hours. 0.408 g of 7,7,8,8-tetracyanoquinodimethane (2 mmol) was added to the mixture which turned an intensive green. The resulting mixture was stirred for 30 minutes and filtered to remove 0.356 g of a purple solid. The tetrahydrofuran solvent of the resulting green-tinted filtrate was removed under reduced pressure. The resulting residue was treated with ether and filtered to remove 0.393 g of green solid. The ether was removed from the resulting filtrate to give 0.402 g of a yellow solid, which was recrystallized from n-butyl chloride to give 0.255 g of octaethyl 1,4-(2,5-cyclohexadienylidene)bis(methylene)tetrakis(phosphonate)(13) (0.347 mmol), mp 82°–84°. Ir(CHCl$_3$) 1523 (C=C), 1245(P=O), and 1041(P—O—C) cm$^{-1}$; UV (tetrahydrofuran $\lambda_{max}(\epsilon)$ 366(48,370) nm; 1H nmr(CDCl$_3$) $\delta$1.38(24, t(J=7 Hz), —OCH$_2$CH$_3$), 3.90–4.4 (16, m, —OCH$_2$—), and 8.14(4, s, =CH=). Anal.: Calcd. for C$_{24}$H$_{44}$O$_{12}$P$_4$: C, 44.45; H, 6.84. Found: C, 44.56; H, 6.75.

EXAMPLE 6

Preparation of Octaethyl 1,4-(2,5-cyclohexadienylidene)bis(methylene)tetrakis(phosphonate)(13) using (Trimethylammoniomethyl)ferricinium Bis(tetrafluoroborate)

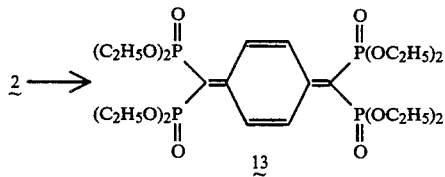

(Trimethylammoniomethyl)ferricinium bis(tetrafluoroborate) was prepared by the following procedure. A slurry of 7.47 g of trimethyloxonium tetrafluoroborate (50.6 mmol) in 125 mL of CH$_2$Cl$_2$ was added to 10 mL of dimethylaminomethylferrocene in 100 mL of the same solvent. The resulting mixture was stirred for 16 hours and the solvent was removed under reduced pressure. The resulting residue was recrystallized from hot water to give 13.62 g of (trimethylammoniomethyl)ferrocene tetrafluoroborate as golden-yellow platelets. 1.32 g of the (trimethylammoniomethyl)ferrocene tetrafluoroborate (8 mmol) were added to a mixture of 0.864 g of p-benzoquinone (8 mmol) and 2.16 mL of 48% aqueous tetrafluoroboric acid (16 mmol) in 60 mL of diethyl ether. The resulting mixture was stirred for 15 minutes and filtered to give a dark blue-black residue which was washed with ether until the washings were colorless to remove quinhydrone and dried under reduced pressure to give 1.69 g of (trimethyl-ammoniomethyl)ferricinium bis(tetrafluoroborate) (3.9 mmol) as a navy-blue solid, which decomposed at high temperature without a characteristic melting point.

40 mL of tetrahydrofuran and four drops of t-butanol were added to 0.080 g of potassium hydride (2 mmol) and 0.650 g of octaethyl 1,4-phenylenebis(methylidyne)tetrakis(phosphonate)(2) (1 mmol). The resulting mixture was warmed to about 60° for 30 minutes, cooled to ambient temperature, and treated with 0.864 g of the (trimethylammoniomethyl)ferricinium bis(tetrafluoroborate) (2 mmol), described above. The resulting combination was stirred until all the blue-black solid reacted and evaporated under reduced pressure. The resulting residue was treated with 7 mL of n-butyl chloride and filtered. The filtrate was diluted with 7 mL of hexane and cooled to $-30°$ to yield 0.275 g of octaethyl 1,4-(2,5-cyclohexadienylidene)bis(methylene)tetrakis(phosphonate)(13) (0.4 mmol).

EXAMPLE 7

Preparation of Dilithium Octaethyl 1,4-Phenylenebis(methylidyne)tetrakis(phosphonate)diide(18) from Octaethyl 1,4-Phenylenebis(methylidyne)tetrakis(phosphonate)(2)

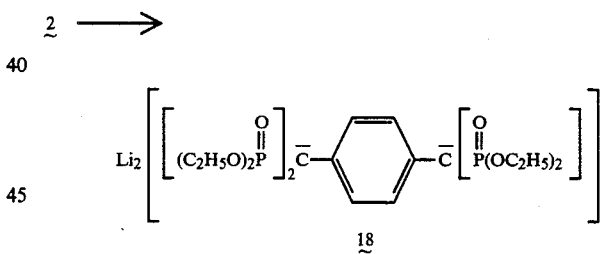

1.40 mL of 1.46N n-butyl lithium (2.2 mmol) in hexane solution were added by syringe to 0.34 mL of 2,2,6,6-tetramethylpiperidine (2 mmol) in 20 ml of dry tetrahydrofuran under nitrogen at $-20°$ to $-30°$. The resulting mixture was allowed to warm to 20°, cooled to $-78°$, and treated with a solution of 0.650 g of octaethyl 1,4-phenylenebis(methylidyne)tetrakis(phosphonate)(2) (1 mmol) in 20 mL dry tetrahydrofuran. The latter solution was prepared under nitrogen and transferred by syringe. The resulting mixture was allowed to warm to 20° and the tetrahydrofuran was removed under reduced pressure. The resulting residue was suspended in ether and filtered in a nitrogen pressure funnel with protection from atmospheric moisture and oxygen to yield 0.639 g of dilithium octaethyl 1,4-phenylenebis(methylidyne)tetrakis(phosphonate)diide(18) (0.95 mmol).

EXAMPLE 8

Preparation of Lithium Octaethyl 1,4-(2,5-cyclohexadienylidene)bis(methylene)tetrakis(phosphonate)(19) from Dilithium Octaethyl 1,4-Phenylenebis(methylidyne)tetrakis(phosphonate)diide(18)

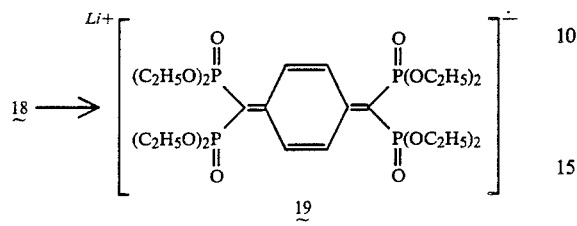

0.273 g of ferricinium tetrafluoroborate (1 mmol) was added to a suspension of 0.662 g of dilithium octaethyl 1,4-phenylenebis(methylidyne)tetrakis(phosphonate)diide(18) (1 mmol) in 10 mL of dry tetrahydrofuran under nitrogen. The resulting mixture was stirred for 15 minutes and filtered with protection from moisture and air in a nitrogen pressure funnel to give 0.329 g of turquoise lithium octaethyl 1,4-(2,5-cyclohexadienylidene)bis(methylene)tetrakis(phosphonate)(19) (0.5 mmol) crystallized as a complex with lithium tetrafluoroborate. Calcd. for $C_{24}H_{44}O_{12}P_4Li_2BF_4$: C, 38.84; H, 5.98; P, 16.69. Found: C, 39.04; H, 6.47; P, 16.55.

EXAMPLE 9

Preparation of Lithium Octaethyl 1,4-(2,5-cyclohexadienylidene)bis(methylene)tetrakis(phosphonate)(19) from Octaethyl 1,4-(2,5-cyclohexadienylidene)bis(methylene)tetrakis(phosphonate)(13) and Dilithium Octaethyl 1,4-Phenylenebis(methylidyne)tetrakis(phosphonate)diide(18)

0.300 g of octaethyl 1,4-(2,5-cyclohexadienylidene)bis(methylene)tetrakis(phosphonate)(13) (0.46 mmol) was dissolved in 10 mL of dry tetrahydrofuran. The resulting solution was added to a suspension of 0.300 g of dilithium octaethyl 1,4-phenylenebis(methylidyne)tetrakis(phosphonate)diide(18) (0.45 mmol) in 10 mL of dry tetrahydrofuran. After 15 minutes, the resulting combination was filtered with a nitrogen pressure funnel with protection from atmospheric moisture and oxygen to give 0.498 g of lithium octaethyl 1,4-(2,5-cyclohexadienylidene)bis(methylene)tetrakis(phosphonate)(19) (0.76 mmol).

EXAMPLE 10

Preparation of Lithium Octaethyl 1,4-(2,5-cyclohexadienylidene)bis(methylene)tetrakis(phosphonate)(19) from Octaethyl 1,4-(2,5-cyclohexadienylidene)bis(methylene)tetrakis(phosphonate)(13)

Octaethyl 1,4-(2,5-cyclohexadienylidene)bis(methylene)tetrakis(phosphonate)(13) and an equivalent amount of N,N,N',N'-tetramethylethylenediamine were placed in dry tetrahydrofuran under nitrogen. An equivalent amount of lithium iodide was added to the resulting solution to form a mixture which was stirred for 15 minutes and filtered according to a procedure similar to that of Example 9 to give lithium octaethyl 1,4-(2,5-cyclohexadienylidene)bis(methylene)tetrakis(phosphonate)(19).

I claim:

1. A compound of the formula

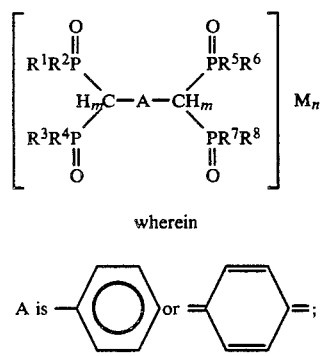

wherein

A is 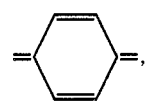

$R^1$, $R^2$, $R^3$, $R^4$, $R^5$, $R^6$, $R^7$, and $R^8$ are individually selected from the group consisting of —F, —Cl, —OH, —OSi(CH$_3$)$_3$, and —OC$_z$H$_{2z+1}$;

and, taken in combination, $R^1$ and $R^2$, $R^3$ and $R^4$, $R^5$ and $R^6$, and $R^7$ and $R^8$ are individually selected from the group consisting of —O(CH$_2$)$_2$O— and —O(CH$_2$)$_3$O—;

provided that, where any two members of $R^1$ through $R^8$ which are attached to the same phosphorus atom are different, said members are —OC$_z$H$_{2z+1}$;

M is Li, Na, K, Rb;

m is 0 or 1; provided that, where A is

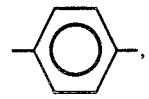

m is 0;

n is 0 where m is 1, 2 where m is 0 and A is

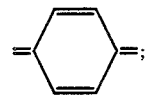

and 0 or 1 where A is

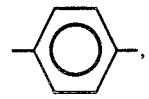

and z is an integer from 2 to 8, inclusive.

2. A compound as described in claim 1, wherein $R^1$ and $R^2$, $R^3$ and $R^4$, $R^5$ and $R^6$, and $R^7$ and $R^8$ are the same.

3. A compound as described in claim 1, wherein $R^1$, $R^2$, $R^3$, $R^4$, $R^5$, $R^6$, $R^7$, and $R^8$ are the same.

4. A compound as described in claim 3, wherein $R^1$, $R^2$, $R^3$, $R^4$, $R^5$, $R^6$, $R^7$, and $R^8$ are alkoxy groups having from 2 to 8 carbon atoms.

5. A compound as described in claim 4, wherein $R^1$, $R^2$, $R^3$, $R^4$, $R^5$, $R^6$, $R^7$, and $R^8$ are ethoxy.

6. A compound as described in claim 5, wherein M is Li.

7. A compound as described in claim 6, wherein m is 0.

8. A compound as described in claim 7, wherein n is 1.

* * * * *